US010335311B1

(12) United States Patent
Altman (10) Patent No.: US 10,335,311 B1
(45) Date of Patent: Jul. 2, 2019

(54) ANTI-SNORING DEVICE (71) Applicant: Barry I. Altman, Staten Island, NY (US)

(72) Inventor: Barry I. Altman, Staten Island, NY (US)

( * ) Notice: Subject to any disclaimer, the term of this patent is extended or adjusted under 35 U.S.C. 154(b) by 0 days.

(21) Appl. No.: 15/994,152

(22) Filed: May 31, 2018

(51) Int. Cl.
A61F 5/56 (2006.01)

(52) U.S. Cl.
CPC .................... A61F 5/566 (2013.01)

(58) Field of Classification Search
CPC ........................................... A61F 5/56
USPC ............................ 128/848, 200.26
See application file for complete search history.

(56) References Cited

U.S. PATENT DOCUMENTS

| 4,114,626 | A | 9/1978 | Beran |
| 4,817,636 | A | 4/1989 | Woods |
| 6,076,526 | A | 6/2000 | Abdelmessih |
| 6,089,232 | A | 7/2000 | Portnoy et al. |
| 7,032,598 | B2 | 4/2006 | Portnoy |
| 7,055,526 | B2 | 6/2006 | Barakat et al. |
| 7,077,138 | B2 | 7/2006 | Bateman et al. |
| 7,156,098 | B2 * | 1/2007 | Dolezal .................. A62B 23/06 128/204.11 |
| 7,640,934 | B2 * | 1/2010 | Zollinger .......... A61M 16/0666 128/200.24 |
| 8,567,406 | B2 | 10/2013 | Chen et al. |
| D777,330 | S | 1/2017 | Kondou |
| 9,795,175 | B2 | 10/2017 | Michalak |
| 2007/0175478 | A1 * | 8/2007 | Brunst .................... A62B 23/06 128/206.18 |
| 2011/0240038 | A1 * | 10/2011 | Doshi .................... A62B 23/06 128/848 |
| 2014/0251335 | A1 | 9/2014 | Black et al. |
| 2016/0278973 | A1 | 9/2016 | Chen et al. |
| 2016/0302961 | A1 * | 10/2016 | Seaman .................... A61F 5/56 |
| 2016/0338870 | A1 | 11/2016 | Walton |

FOREIGN PATENT DOCUMENTS

WO    WO0232350    4/2002

OTHER PUBLICATIONS

Chin-Up Strip, The Chin-Up Strip Company, Dacula, GA, accessed at http://chinupstrip.com on May 30, 2018.

(Continued)

Primary Examiner — Keri J Nelson
(74) Attorney, Agent, or Firm — Gerald E. Hespos; Michael J. Porco; Adam Hotzoglou (57) ABSTRACT The present disclosure is directed to an anti-snoring device. The anti-snoring device of the present disclosure includes an elastic, adhesive sheet for gently drawing the mouth of a user to a substantially closed position while the anti-snoring device is worn by the user. The elastic adhesive sheet is attached via adhesive backing to the user's skin and extends from just below the user's nose to just below the user's chin. A breathing tube of the anti-snoring device extends through the adhesive sheet and into the user's mouth to enable the user to breathe through their mouth while the elastic sheet maintains the user's mouth in a substantially closed position. The end of the breathing tube that is mounted to the adhesive sheet terminates at the side of the adhesive sheet oriented away from the user.

20 Claims, 11 Drawing Sheets (56) References Cited

OTHER PUBLICATIONS

Woody Knows Disposable Mouth Strips; http://woodyknows.com/mouth-dryness-sore-throat-amp-snoring-solution-woodyknows-disposable-mouth-strips-mouth-tape-gently-close-your-mouth-to-relieve-mouth-breathing-and_p0886.html, accessed on May 30, 2018.
SomniFix Mouth Strips; https://somnifix.com/products/mouth-strips-snoring-sleep-aid, accessed on May 30, 2018.

\* cited by examiner

ANTI-SNORING DEVICE

FIELD

The present disclosure generally relates to anti-snoring devices, and more particularly, to a non-intrusive anti-snoring device for substantially closing a user's mouth, while concurrently allowing the user to breathe through their mouth.

BACKGROUND

Figure 1:
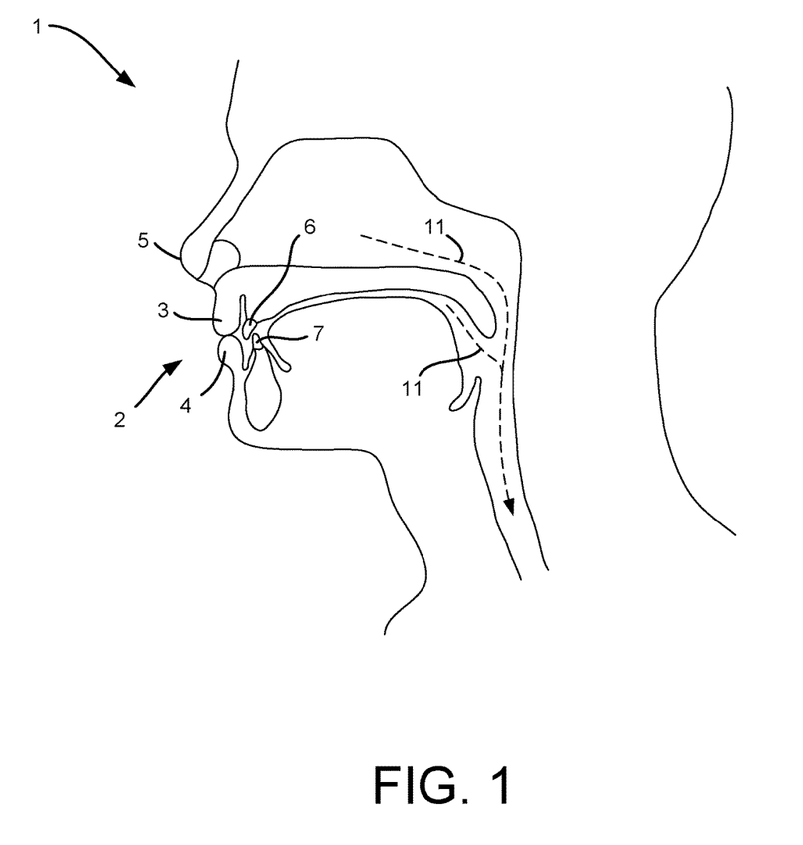
FIG. 1 is a partial side cross-section view of the head of a human in accordance with the present disclosure.

Referring to FIG. 1, a partial side cross-section view of the head of a human 1 is shown in accordance with the present disclosure. During natural breathing processes, air inhaled/exhaled via openings in the mouth 2 and/or nose 5 is provided via corresponding air passageways 11 to/from the lungs. For many adults and children, breathing while sleeping may result in snoring. The audible sound resulting from snoring is caused by the vibration of tissue, such as, the soft palate and/or uvula, disposed along air passages 11 of the respiratory structures. One of the main causes of snoring is the opening of the mouth 2 while sleeping. When the mouth 2 is opened while sleeping, and the lower jaw is moved away from the upper jaw, tissue disposed along the air passages 11 may collapse over the air passages 11 and vibrate as air moves through, which causes the snoring sound. The snoring sound due to the collapsing of the air passages 11 may wake individuals within the vicinity of a snorer. Also, if the air passages 11 collapse completely, the snorer may be unable to breathe and forced to abruptly wake up, thus disturbing the snorer's sleep.

While many devices attempt to reduce the act of snoring by closing mouth 2 or maintaining the air passageways 11 open via various means, these devices suffer from many disadvantages, including being ineffective, uncomfortable, bulky, and/or expensive.

For example, continuous positive airway pressure (CPAP) devices are expensive, uncomfortable, bulky, and loud. CPAP devices use air compressors to provide air to a mask worn over the mouth 2 and nose 5 of the user 1 via a flexible hose. The air compressor makes continuous noise throughout the duration of the user's sleep as the air compressor is constantly maintaining a suitable pressure to support air delivery to the mask. Furthermore, the mask worn by the user 1 and corresponding hose attached to the mask necessitate that the user 1 wear uncomfortable components (e.g., the mask and hose) that protrude from the user's face. The mask and tube effect the user's ability to find a comfortable sleeping position and also provide a barrier between the user 1 and another individual, such as the user's spouse, sleeping proximately to the user. For example, a user 1 that prefers to sleep on their stomach, may be prevented from doing so while wearing a CPAP device because of the components of the CPAP device that protrude from the user's mouth and nose. Additionally, due to the size of CPAP devices, CPAP devices are inconvenient for transport when the user 1 is not sleeping at their normal residence and is travelling.

Any devices that are worn by a user to introduce or otherwise regulate gases and/or fluids (e.g., aiding inhalation by providing pressurized air, aiding exhalation by providing suction, etc.) while the user sleeps suffer from the deficiencies described above (e.g., protruding from the user's face, being uncomfortable, etc.) Another deficiency of devices that introduce or otherwise regulate gases and/or fluids via the user's mouth or nose, is the concern associated with a component failure in these devices. If a component fails while the user is sleeping, the device may no longer be able to aid in the user's sleep by delivering or regulating gases and/or fluids. Additionally, the fluids and/or gases introduced or regulated may become dangerous to the user upon a failure to be properly regulated, thus increasing the liability to the manufacturers and/or sellers of these devices. In general, the complexity of these devices introduces many points of failure and liabilities.

As another example, several devices, such as chinstraps and others, exist that attempt to reduce snoring by forcing the mouth 2 of the user 1 closed throughout the duration of the user's sleep. These mouth-closing devices also suffer from several disadvantages. For example, these mouth-closing devices often apply aggressive pressure to the lower jaw of the user 1 to force the lower jaw toward the upper jaw, thus maintaining the mouth in a closed state. This aggressive pressure may cause soreness for the user 1 about the user's jaw and other structures surrounding the jaw.

Additionally, these mouth-closing devices, like CPAP devices, may be bulky, including several components that protrude from the user's mouth, nose, or head. These components may prevent the user 1 from finding a comfortable sleeping position, for example, as stated above, in the scenario where the user 1 prefers to sleep on their stomach with their face oriented toward their pillow or mattress, these components prevent the user 1 from sleeping in this position. For users who change positions while sleeping, these protruding components may be caught on the user's pillow, pillow sheets, bed sheets, blankets, etc. while the user 1 attempts to change sleeping positions. Also, for users who sleep proximately to another individual, such as their spouse, these protruding components may prevent this proximity and/or interfere with the other individual's sleep.

Another major disadvantage of these mouth-closing devices is that they prevent and/or make it difficult for the user 1 to inhale and/or exhale any air from the user's mouth 2. Preventing a user 1 from breathing from their mouth 2 will cause a major impediment for many individuals while sleeping. Many individuals simply cannot receive enough air through nose to fully support the breathing processes that the body requires. This may be due to obstructions in the pathways of the nose, for example, because of congestion or abnormal tissue protrusions creating overly narrow air passages. Furthermore, many individuals simply are more comfortable inhaling/exhaling some or all of the air in the breathing process via their mouths. Since, for uninterrupted, restful sleep to occur, a certain level of comfort is required, preventing a user 1 that is more comfortable breathing through their mouth from breathing through their mouth during sleep will also prevent the user 1 from achieving uninterrupted, restful sleep.

Although some of these mouth-closing devices attempt to include provisions for breathing through the user's mouth, these provisions are ineffective. For example, some of these mouth-closing devices may leave a portion of the user's lips 3, 4 exposed in an attempt to enable some degree of breathing via the user's mouth while the user 1 is wearing the mouth-closing device during sleep. However, as shown in FIG. 1, when the mouth 2 is caused to remain in a closed position via one of these mouth-closing devices, the lips 3, 4 of the user 1 come into contact and completely seal the user's oral cavity, thus creating a closed pressure system within the user's oral cavity. Therefore, with lips 3, 4 being held in contact by the mouth-closing device, if the user 1 attempts to inhale air via the mouth 2, the lips 3, 4 are drawn toward the interior of the oral cavity, but the lips 3, 4 are prevented from parting to allow the entry of air into the oral cavity by the teeth 6, 7 and surround structures to the teeth 6, 7 (e.g., the gums) of the user, which sit behind the lips 3, 4 within the oral cavity. Thus, while the mouth 2 is held completely closed by the mouth-closing device and the lips 3, 4 are in contact, the user 1 cannot inhale air via their mouth 2. Furthermore, exhaling air is also very difficult with the mouth 2 being completely closed by the mouth-closing device and lips 3, 4 being in contact with each other. When an attempt is made to exhale air via mouth 2, the contacting lips 3, 4 resist the exit of air via the mouth 2 and any air that is released will result in the vibration of the lips 3, 4, which causes a clapping sound resulting from the lips 3, 4 repeatedly hitting each other. Thus, while the mouth 2 is held completely closed by the mouth-closing device and the lips 3, 4 are in contact, the user 1 cannot easily exhale air via their mouth 2 and when air is exhaled via the mouth 2 an audible sound is generated.

Another provision sometimes included in these mouth-closing devices to attempt to allow a user 1 some degree of mouth breathing while wearing the mouth-closing device is to enable the device to stretch or otherwise expand, such that the user 1 can part their lips 3, 4 while wearing the device. However, this provision requires a conscious, voluntary act of the user 1 to resist, and partially overcome, the force that the mouth-closing device is exerting on the lower jaw to cause the mouth 2 of the user 1 to close. This conscious, voluntary act of the user 1 causes the user 1 to wake up from the user's unconscious, sleeping state. Therefore, this provision is not effective in enabling the user 1 to breathe through the user's mouth 2 while wearing one of these mouth-closing devices.

In light of the disadvantages of existing devices for reducing and/or preventing snoring, a need exists for an anti-snoring device that is effective while also being comfortable and non-intrusive to the user's natural sleeping habits (e.g., sleeping position and/or sleeping proximately to other individuals).

SUMMARY

In one aspect of the present disclosure, an effectively engineered, external, non-orally-obtrusive anti snoring/sleep apnea device, to be self-applied by a user over the user's mouth, is provided. The anti-snoring device is made of a hypoallergenic fabric-woven material including an adhesive backing. A gauze pad is coupled to a portion of the adhesive backing. When applied to the user's face, the adhesive backing spans from just below the bottom bridge of the user's nose adhering to the area of skin above the upper lip of the user, then bridging over the upper and lower lips of the user with the gauze pad adjacent to the user's lips, continuing down the chin, wrapping and ending just below the under-chin jaw of the user and adhering thereto. The mouth closing influence of the anti-snoring device keeps the air passages of the user open, preventing excessive open mouth breathing and subsequent vibration of such airways from their closings, known as snoring and interrupted sleep-apnea. However, for many individuals, effective sleep and snoring prevention cannot be achieved by nasal breathing alone, since proper air intake can only be achieved with partial assisted mouth breathing while simultaneously maintaining mouth closure. This simultaneous action is achieved by introducing a non-contaminant, bisphenol A (BPA) free, polystyrene tube. The tube extends from the hypoallergenic fabric-woven material and is inserted through the gauze pad area and user lips, only penetrating the mouth by slightly parting the lips of the user and stopping just at the front user's teeth. This airflow passage tube is held in place by a flush-mounted round ring that rests flat along and outside the external surface of the hypoallergenic fabric-woven material. A high efficiency particulate air (HEPA) air filter is mounted within the tube to prevent fine dirt, dust, airborne pollutant entry into the tube while the user is breathing. The tube can be adjusted for length by means of its incorporated accordion-telescoping section. The over-the-lip gauze pad section may be treated with non-allergenic flavored melatonin for lip moisture absorption to aid in natural sleep inducement.

BRIEF DESCRIPTION OF THE DRAWINGS

The above and other aspects, features, and advantages of the present disclosure will become more apparent in light of the following detailed description when taken in conjunction with the accompanying drawings in which:

FIG. 2C is a front perspective view of the anti-snoring device of FIG. 2A in accordance with an embodiment of the present disclosure;

It should be understood that the drawing(s) are for purposes of illustrating the concepts of the disclosure and is not necessarily the only possible configuration for illustrating the disclosure.

DETAILED DESCRIPTION

Embodiments of the present disclosure will be described herein below with reference to the accompanying drawings. In the following description, well-known functions or constructions are not described in detail to avoid obscuring the present disclosure in unnecessary detail. The word "exemplary" is used herein to mean "serving as an example, instance, or illustration." Any configuration or design described herein as "exemplary" is not necessarily to be construed as preferred or advantageous over other configurations or designs. Herein, the phrase "coupled" is defined to mean directly connected to or indirectly connected with through one or more intermediate components.

The present disclosure is directed to an anti-snoring device. The anti-snoring device of the present disclosure is configured with an elastic adhesive sheet for gently drawing the mouth of a user to a substantially closed position while the anti-snoring device is worn by the user. The elastic adhesive sheet is attached via adhesive backing to the user's skin and extends from just below the user's nose to just below the user's chin. A breathing tube of the anti-snoring device extends through the adhesive sheet and into the user's mouth to enable the user to breathe through their mouth while the anti-snoring device is worn. The end of the breathing tube that is mounted to the adhesive sheet terminates at the side of the adhesive sheet oriented away from the user, such that the breathing tube is prevented from being caught on objects disposed proximately to where the user sleeps, interfering or otherwise contacting an individual sleeping proximately to the user, and interfering with sleeping positions preferring by the user (e.g., sleeping on the user's stomach). While being worn by the user, the anti-snoring device of the present disclosure enables the user to breathe through one or both of the user's mouth and nose, while also keeping the mouth substantially closed. Thus, the anti-snoring device of the present disclosure is an efficient, convenient, cost-effective, and nonobtrusive means by which to prevent snoring for the user.

Figure 2A:
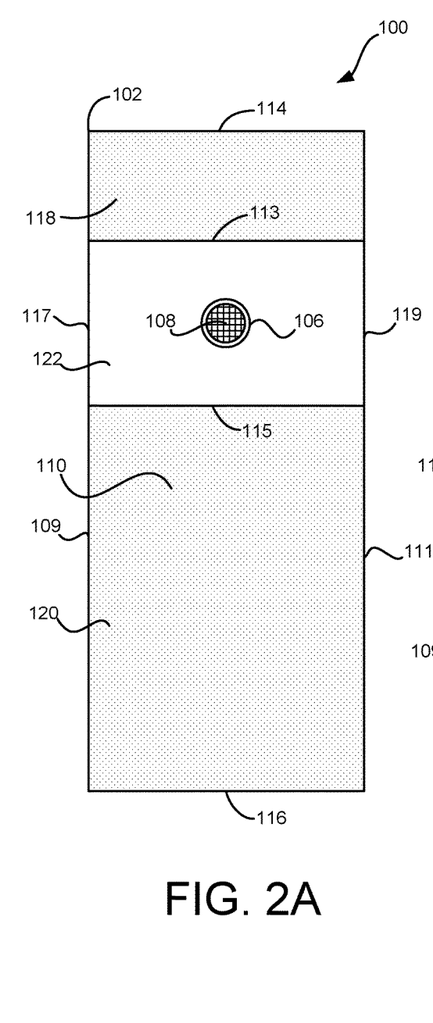
FIG. 2A is a front view of an anti-snoring device in accordance with an embodiment of the present disclosure.
Figure 2B:
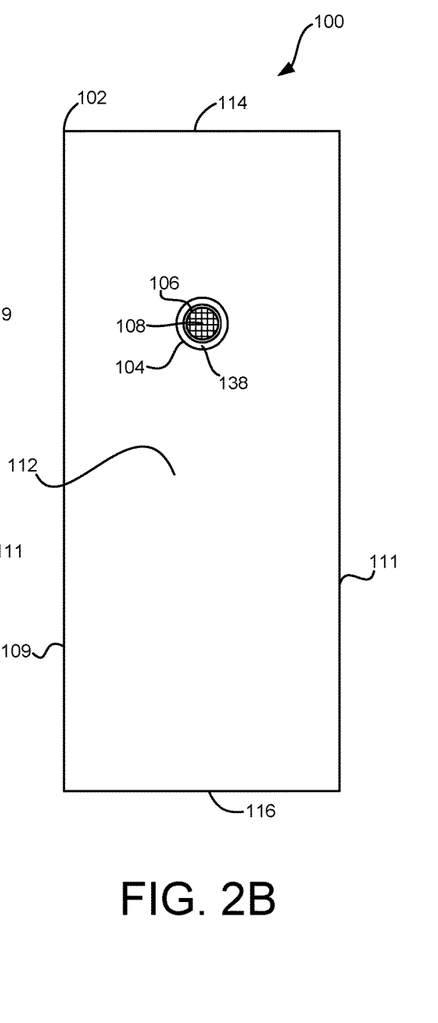
FIG. 2B is a rear view of the anti-snoring device of FIG. 2A in accordance with an embodiment of the present disclosure.
Figures 2D, 2E:
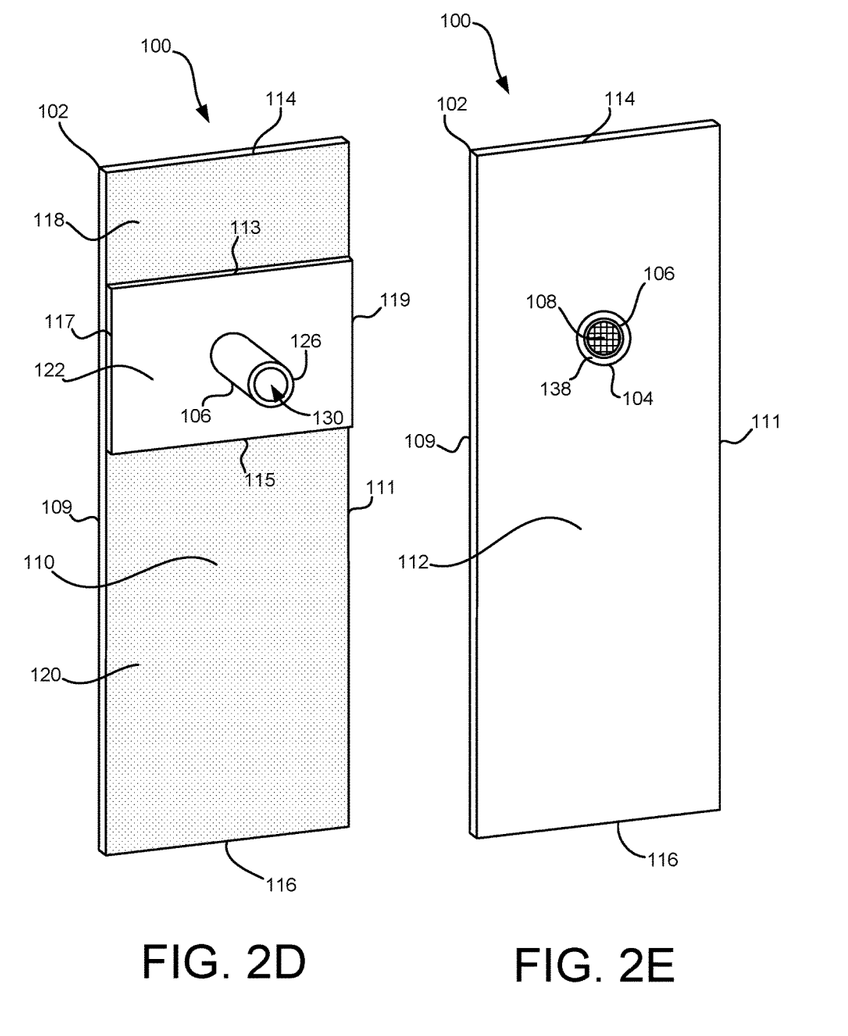
FIG. 2D is a rear perspective view of the anti-snoring device of FIG. 2A in accordance with an embodiment of the present disclosure.
Figures 2F, 2G, 2H, 2I:
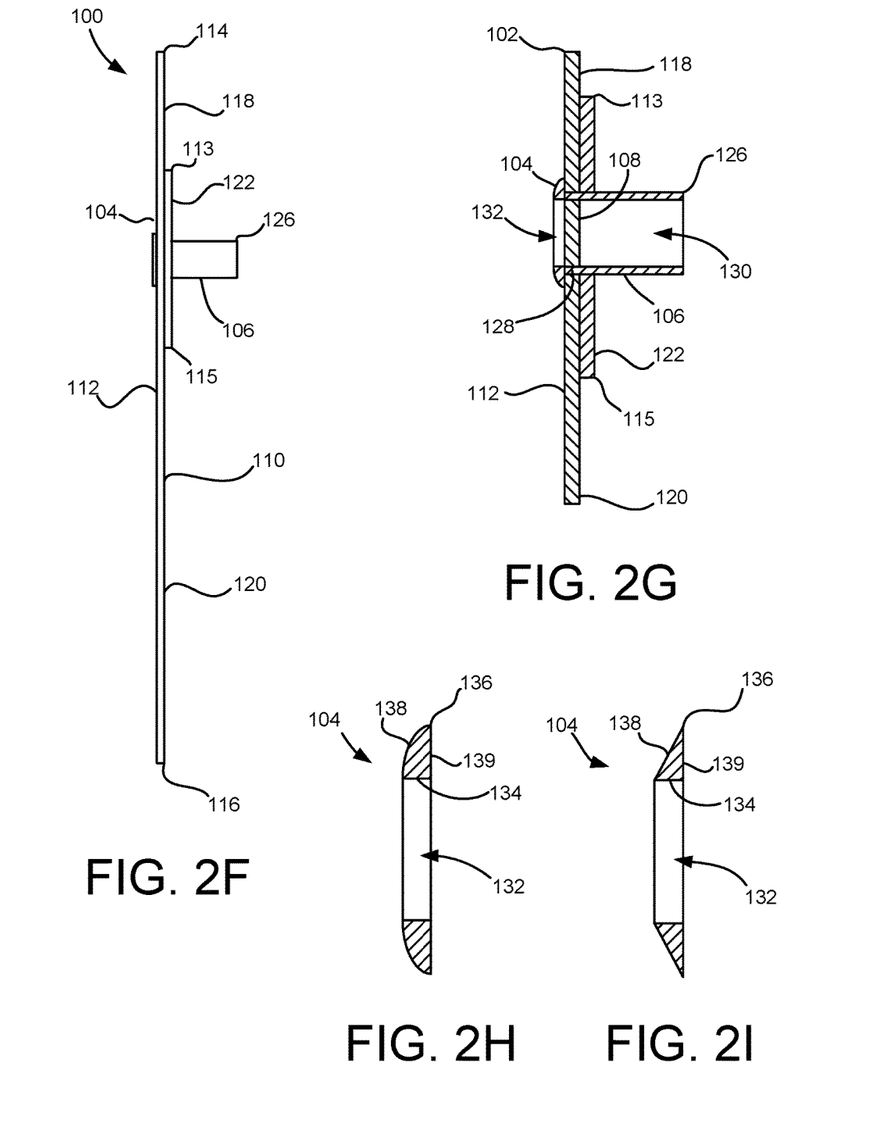
FIG. 2F is a side view of the anti-snoring device of FIG. 2A in accordance with an embodiment of the present disclosure.
FIG. 2G is a partial cross-section view of the anti-snoring device of FIG. 2A in accordance with an embodiment of the present disclosure.
FIG. 2H is a cross-section view of a mounting disk of the anti-snoring device of FIG. 2A in accordance with an embodiment of the present disclosure.
FIG. 2I is a cross-section view of an alterative mounting disk for the anti-snoring device of FIG. 1 in accordance with an embodiment of the present disclosure.

Referring to FIGS. 2A-2G, an anti-snoring device 100 is shown in accordance with the present disclosure, where FIG. 2A is a front view, FIG. 2B is a rear view, FIGS. 2D and 2E are perspective views, FIG. 2F is a side view, and FIG. 2G is a side partial cross-section view of the anti-snoring device 100.

Device 100 includes an elastic adhesive sheet or pad 102, mounting disk 104, breathing tube 106, filter 108, and a non-adhesive sheet or pad 122. Sheet 102 includes a top end 114, a bottom end 116, opposite edges 109, 111, and opposite sides 110, 112. Sheet 102 is made of a skin sensitive, hypoallergenic, flexible and elastic material. In one embodiment, the elastic material is a woven fabric. In other embodiments, the elastic material may be a plastic (e.g., polyethylene, polyurethane, etc.) or a latex. In some embodiment, the elastic material may be waterproof or moister-resistant. The elasticity of sheet 102 enables sheet 102 to be elastic in all directions, while the flexibility of sheet 102 enables sheet 102 to conform to the varying shapes and geometries of different users' faces. Side 110 of sheet 102 is configured with adhesive portions 118, 120, where adhesive portion 118 is disposed toward top end 114 and adhesive portion 120 is disposed toward bottom end 116. Non-adhesive pad 122 includes top end 113, bottom end 115, and edges or sides 117, 119. Non-adhesive pad 112 is fixedly coupled to side 110 of sheet 102 between adhesive portions 118, 120. In one embodiment, non-adhesive pad 112 is made of a soft (i.e., non-abrasive to the skin), fluid-absorbent material, such as, cotton, and is configured in a weave, such as, gauze.

As best seen in FIG. 2G, tube 106 includes ends 126, 128 and a hollow interior 130, where hollow interior 130 extends from end 126 to end 128 of tube 106. End 128 of tube 106 is disposed through aligning openings or apertures in adhesive sheet 102 and non-adhesive pad 122, where each aperture has substantially the same circumference and diameter as the outer circumference and diameter of tube 106. End 128 of tube 106 is mounted to adhesive sheet 102 via mounting disk 104, such that end 128 substantially terminates at side 112 of adhesive sheet 102 and end 126 of tube 106 extends substantially perpendicularly away from non-adhesive pad 122 and side 110 of adhesive sheet 102. In one embodiment, tube 106 is made of a polystyrene non-allergenic BPA (Bisphenol A) contaminant free material. In some embodiments, tube 106 is disposed directly through the center of pad 122 (i.e., equidistant from ends 113, 115 and edges 117, 119). In other embodiments, tube 106 is disposed through pad 112 more proximately to end 113 than end 115 while being equidistant from edges 117, 119.

Mounting disk 104 includes an aperture or opening 132 configured to align with the opening to hollow interior 130 of tube 106. As best seen in FIG. 2H, mounting disk 104 also includes a substantially planar side or surface 139 configured to be coupled (e.g., via glue splicing or other securing means) to side 112 of sheet 102 and end 128 of tube 106. Mounting disk 104 includes an inner circumference 134 and an outer circumference 136 and an edge or surface 138 (opposite to side or surface 139,) which extends from inner circumference 134 to outer circumference 136. Tapering edge 138 tapers or converges toward outer circumference 136 from inner circumference 134, such that the end of edge 138 at outer circumference 136 is disposed more proximately to side 112 of sheet 102 than the end of edge 138 at inner circumference 138.

In one embodiment, edge 138 is configured to be curved (e.g., in a convex shape), as shown in FIG. 2H, while in other embodiments, edge 138 is configured to be substantially planar, as shown in FIG. 2I. The inner circumference 134 of disk 104 is configured to be less than the outer circumference of tube 106, while the outer circumference 126 of disk 104 is configured to be greater than the outer circumference of tube 106, such that surface 139 of disk 104 can be simultaneously coupled to side 112 of sheet 102 and end 128 of tube 106. In one embodiment, the diameter of inner circumference 134 is configured to be substantially the same as the diameter of the inner circumference of tube 106. In one embodiment, the diameter of outer circumference 136 is 0.5 inches, the diameter of inner circumference 134 is 0.25 inches, the diameter of the outer circumference of tube 106 is $5/16^{th}$ of an inch, and the diameter of the inner circumference of tube 16 is 0.25 inches.

Figure 2J:
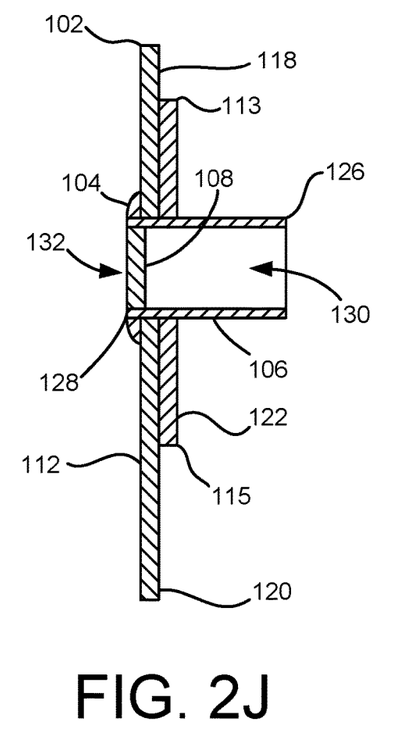
FIG. 2J is another partial cross-section view of the anti-snoring device of FIG. 2A in accordance with an embodiment of the present disclosure.

In another embodiment, the outer circumference of tube 106 is coupled to the inner circumference 134 of mounting ring 104. For example, this embodiment is shown in FIG. 2J. As shown in FIG. 2J, in this embodiment, end 128 of tube 106 extends into aperture 132 of mounting ring 104 and slightly past side 112 of sheet 102.

In either case, as shown in FIGS. 2A-2G and 2J, a circular filter 108 having substantially the same circumference and diameter as the inner circumference and diameter of tube 106 is mounted to the inner circumference of tube 106 proximately to the end 128. Filter 108 is configured as a high efficiency particulate air (HEPA) filter for filtering airborne molecular mold or other air impurities. In one embodiment, the diameter of filter 108 is 0.25 inches and the thickness of filter 108 is between $\frac{1}{8}^{th}$ and $\frac{1}{16}^{th}$ of an inch.

Figure 3A:
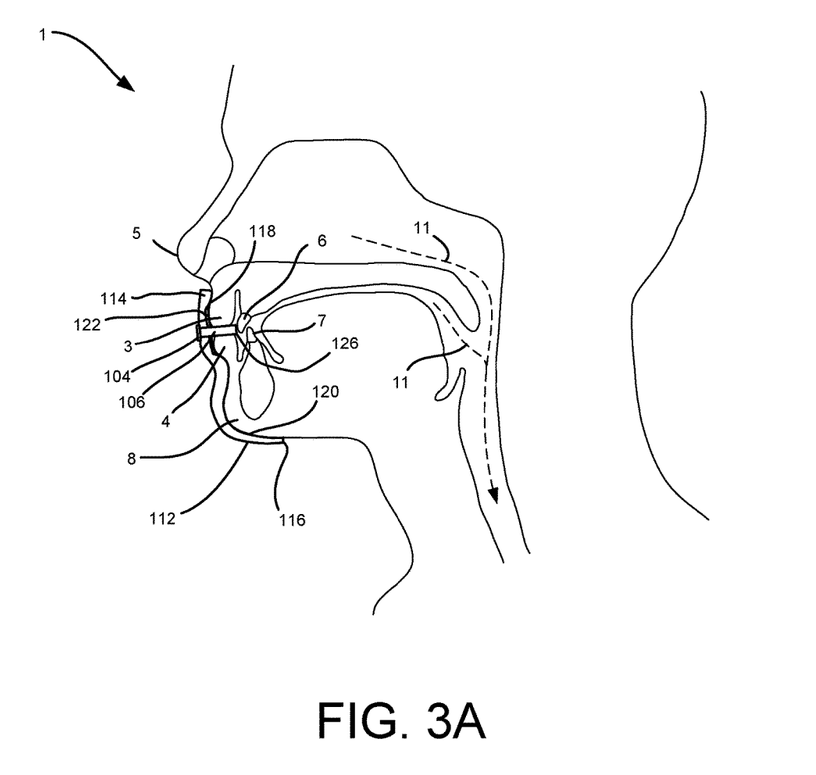
FIG. 3A is a side cross-section view of the anti-snoring device of FIG. 2A being worn by a human in accordance with an embodiment of the present disclosure.
Figure 3B:
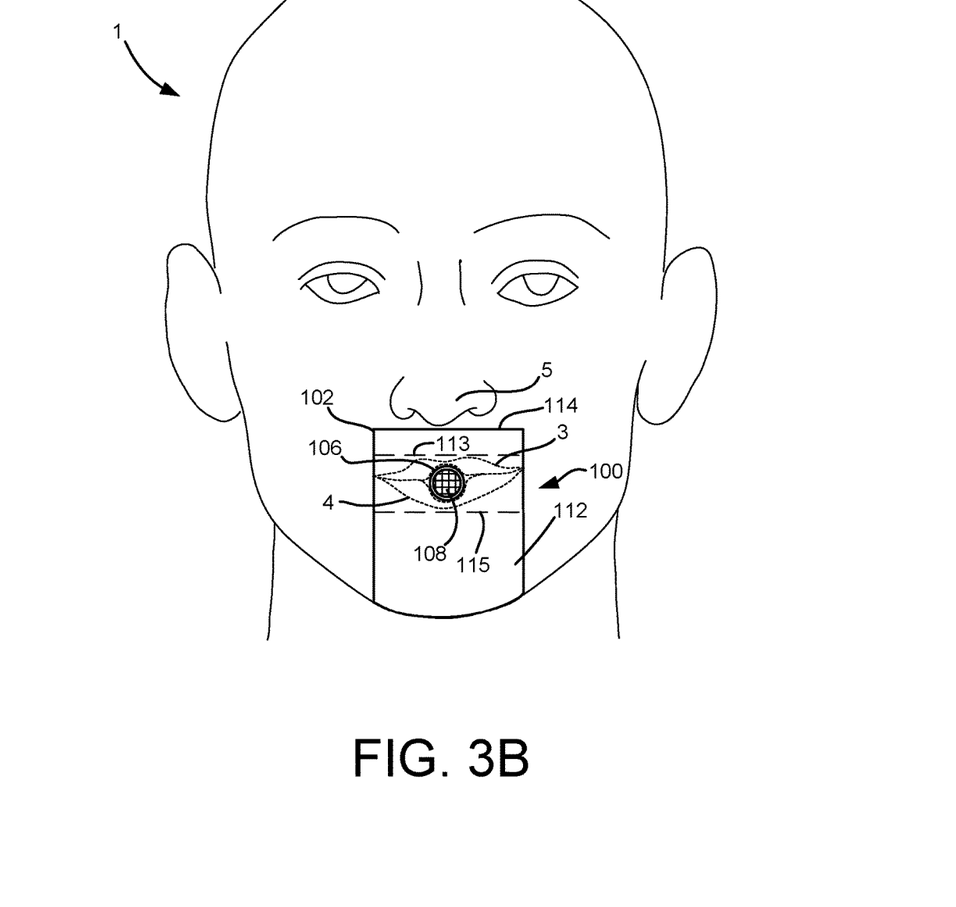
FIG. 3B is a front view of the anti-snoring device of FIG. 2A being worn by a human in accordance with an embodiment of the present disclosure.

Referring to FIGS. 3A and 3B, anti-snoring device 100 is shown being worn by a user 1 in accordance with the present disclosure. In use, side 110 of device 100 is disposed over mouth 2 of user 1, such that the adhesive portion 118 adheres to the skin of the user 1 above the upper lip 3 and below the nose 5 (i.e., the mustache area) and the adhesive portion 120 adheres to the skin of the user 1 below the lower lip up until just below (or just past) the chin 8. As shown in FIG. 3A, the elastic flexible sheet 102 conforms to the contours of the user's face (e.g., lips, chin, etc.) in a form-fitting manner. While device 100 is coupled to the user's face, non-adhesive pad 122 is disposed over the user's lips 3, 4 and tube 106 extends into the user's mouth between lips 3, 4. As best seen in FIG. 3A, the length of tube 106 (from end 128 to end 126) is dimensioned such that end 126 extends into the oral cavity of the user 1 and stops or terminates just before the user's teeth 6, 7. Furthermore, as best seen in FIG. 3B, the outer diameter and circumference of tube 106 is chosen to be sufficiently small to enable lips 3, 4 of user 1 to be in a substantially closed state (e.g., 90% or more closed) around the outer circumference of tube 106. The elastic material of adhesive sheet 102 is configured to gently draw or guide the lower jaw of user 1 toward the upper jaw, such that the lips 3, 4 of mouth 2 are drawn together and remain in a substantially closed state around tube 106.

Anti-snoring device 100 is configured with several features that overcome the limitations of prior art devices described above and make device 100 a very effective means by which to reduce and substantially prevent snoring in an unobtrusive manner to the user. The elastic and flexible fabric or material of sheet 102 is configured to gently maintain the lips 3, 4 of the user's mouth 2 in a substantially closed state around the outer circumference of tube 106, such that the main cause (i.e., a substantially open mouth 2) of snoring is eliminated. While the user's mouth 2 is gently maintained in the substantially closed state by sheet 102, the breathing tube 106 that is inserted into the user's mouth 2 enables the user 1 to breathe through their mouth 2 via the hollow interior 130 of tube 106. Any air breathed through tube 106 is filtered via filter 108, thus preventing airborne molecular mold or other impurities from being inhaled by the user. The length of tube 106 is selected such that end 126 of tube 106 terminates at or before the user's teeth 6, 7, in this way, the user's upper and lower jaws are enabled to remain as close as possible during sleep because teeth 6, 7 are not parted. For example, in one embodiment, the length of tube 106 from end 126 to end 128 is 0.75 inches. Since the user's mouth 2 is guided or drawn in a substantially closed state, the air passages 11 of the user 1 remain as open as possible to reduce any vibration in the tissue disposed along passages 11 that normally produce the snoring sound when passageways 11 collapse. Furthermore, since sheet 102 does not cover the user's nose 5, the user 1 may breathe through the user's nose 5 in addition to, or in lieu of, any breathing occurring through the user's mouth 2.

Additionally, each of the components of device 100 are dimensioned to minimize any protrusions from device 100 from the user's face while device 100 is worn. For example, sheet 102 and pad 122 are configured with a minimum thickness, where in one embodiment sheet 102 has a thickness of $\frac{1}{16}^{th}$ of an inch. Furthermore, end 128 of tube 106 is mounted to sheet 102 via mounting disk 104 such that end 128 terminates at side 112 of sheet 102. In this way, tube 106 does not protrude from side 112 of sheet 102 and cannot interfere with the user's sleep (i.e., by getting caught on a material or object proximate to the user's sleeping location, preventing the user 1 from achieving comfortable sleeping positions, and/or interfering or contacting an individual the user 1 is sleeping proximately too). Also, mounting disk 104 is configured with a minimum thickness and with a tapered edge 138, which tapers from inner circumference 134 of disk 104 to outer circumference 136 of disk 104. The minimum thickness and tapering edge 138 of disk 104 is configured to prevent materials and objects that come into contact with side 112 of sheet 102 from being caught on disk 104.

Also, the various lengths of widths of sheet 102 and pad 122 are selected to optimize the performance of anti-snoring device 100 while also minimizing the needed size and invasiveness of device 100. The length of adhesive sheet 102 from end 114 to end 116 is selected such that adhesive sheet 102 extends from just below the nose 5 of user 1 to just below the chin 8 of user 1. For example, in one embodiment, the length of adhesive sheet 102 from end 114 to end 116 is 4.75 inches. The width of adhesive sheet 102 from edge 109 to edge 111 is selected such that adhesive sheet 102 extends approximately from one side of lips 3, 4 to the other side of lips 3, 4 (i.e., the edges where lips 3, 4 meet). For example, in one embodiment, the width of sheet 102 from edge 109 to edge 111 is 1.75 inches.

The length of non-adhesive pad 122 from end 113 to end 115 and the width of non-adhesive pad 122 from edge 117 to edge 119 are selected such that pad 122 substantially covers lips 3, 4 of the user 1 without extending very far past lips 3, 4 in any direction (i.e., the total area of pad 122 is minimized, while still covering the user's lips 3, 4). For example, in one embodiment, the length of non-adhesive pad 122 from end 113 to end 115 is 1.25 inches and the width of non-adhesive pad 122 from edge 117 to edge 119 is 1.75 inches. Since the length and width of pad 122 cover the user's lips 3, 4, the soft, non-abrasive material of pad 112 protects the sensitive tissue of lips 3, 4. As described above, in some embodiments, tube 106 is disposed through pad 112 more proximately to end 113 than end 115 while being equidistant from edges 117, 119. In this way, there is additional length between the outer circumference of tube 106 and end 115 of non-adhesive pad 112 than between the outer circumference of tube 106 and end 113 to take into account the larger size of the lower lip 4 than the upper lip 3 of most user's.

The length of adhesive portion 118 from end 114 of sheet 102 to end 113 of pad 122 is selected such that adhesive portion 118 extends from just below the user's nose 5 to just above the user's upper lip 3. For example, in one embodiment, the length of adhesive portion 118 is 0.5 inches. Since the length of adhesive portion 118 is selected such that end 114 terminates just below the user's nose, the openings in the user's nose 5, are not covered or obstructed and the user 1 can breathe through their nose 5 while device 100 is worn by the user 1. Furthermore, since the length of adhesive portion 118 is selected such that end 114 terminates just above the user's upper lip 3, the adhesive portion 118 does not contact the user's upper lip 3, and therefore, when device 100 is removed from the user's face, the sensitive tissue of upper lip 3 is sparred from the discomfort of removing adhesive material therefrom.

The length of adhesive portion 120 from end 116 of sheet 102 to end 115 of pad 122 is selected such that adhesive portion 120 extends from just below the user's lower lip 5 to just below the user's chin 8. For example, in one embodiment, the length of adhesive portion 120 is 3 inches. Since the length of adhesive portion 120 is selected such that the end of adhesive portion adjacent to end 115 pad 122 terminates just below the user's lower lip 5, the adhesive portion 120 does not contact the user's lower lip 5, and therefore, when device 100 is removed from the user's face, the sensitive tissue of lower lip 5 is sparred from the discomfort of removing adhesive material therefrom.

It is to be appreciated that all lengths, widths, diameters, circumferences, and/or any other dimension of device 100 is merely exemplary and that other dimensions may be used without deviating from the scope of the present disclosure. In some embodiments, the dimensions of device 100 may be altered to provide small, medium, large, and/or other sizes to accommodate, children and/or other individuals having different geometries defining their facial and oral features.

Figure 4:
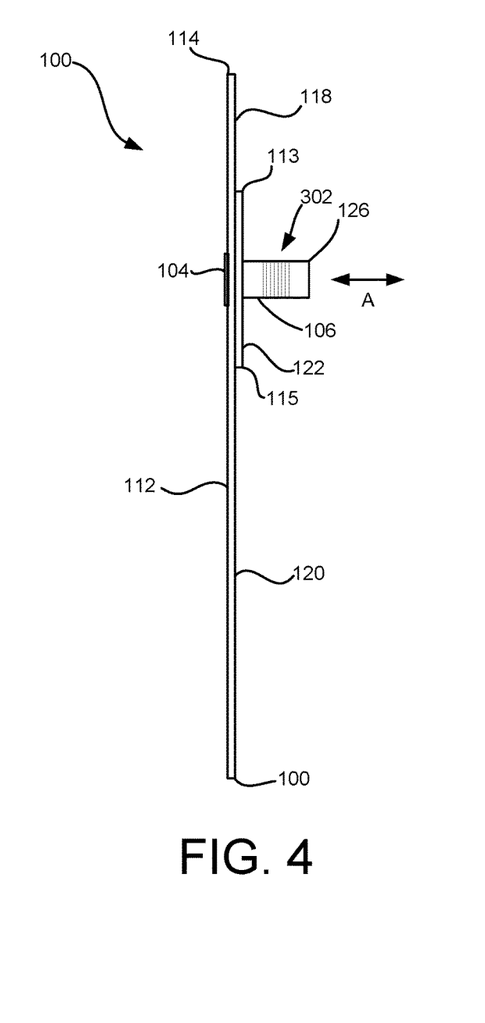
FIG. 4 is a side view of an anti-snoring device with an extendible breathing tube in accordance with an embodiment of the present disclosure.

In one embodiment, tube 106 is configured to be extendable away from and retractable toward side 110 of adhesive sheet 102, such that the length of tube 106 may be adjusted as desired. For example, referring to FIG. 4, tube 106 is shown with a telescoping section 302 configured to enable tube 106 to be extendable and retractable relative to side 110 of sheet 102 along a direction A. In one embodiment, telescoping section 302 includes a plurality of folds configured as a concertina-type hinge to enable tube 106 to be extendable and retractable along direction A. The folds in telescoping section 302 may also enable a portion of tube 106 disposed toward end 128 to be bent or pivoted relative to a portion of tube 106 disposed toward end 126 about telescoping section 302. In this way, telescoping section 302 is configured to enable a user to choose the length of tube 106 and the angle the end 126 of tube 106 extends into the mouth 2 of user 1 relative to end 128 of tube 106, such that end 126 of tube 106 is adaptable for use for the varying geometries of different individuals (i.e., different distances between an individual's lips 3, 4 and teeth 6, 7, etc.)

Figure 5:
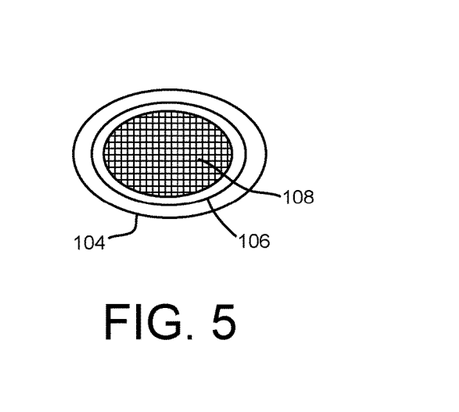
FIG. 5 illustrates a substantially elliptical filter, breathing tube, and mounting disk for an anti-snoring device in accordance with an embodiment of the present disclosure.

Although in the embodiments of above, mounting disk 104, tube 106, and filter 108 are shown and described as being substantially circular in shape, in other embodiments, disk 104, tube 106, and filter 108 may be configured in a substantially elliptical shape. For example, referring to FIG. 5, disk 104, tube 106, and filter 108 are shown configured with a substantially elliptical shape in accordance with an embodiment of the present disclosure. The elliptical shape means that each of disk 104, tube 106, and filter 108 are configured with two diameters, wherein a first diameter of the two diameters is greater than a second diameter of the two diameters. In this embodiment, the second (shorter) diameter of each of disk 104, tube 106, and filter 108 is aligned lengthwise along sheet 102 from end 114 to end 116 and the first (longer) diameter is aligned widthwise along sheet 102 from edges 109, 111. The second (shorter) diameter of each of disk 104, tube 106, and filter 108, while configured in the elliptical shape, enables the lengthwise diameter of tube 106 to be shorter than the circular shape of previous embodiments, thus requiring the lips 3, 4 of the user 1 to be parted even less to receive end 126 of tube 106. The first (longer) diameter of tube 106, while configured in the elliptical shape, enables the widthwise diameter of tube 106 to be longer than the circular shape of pervious embodiments, thus enabling the total area of the opening into hollow interior 130 of tube 106 to remain the same despite the shorter lengthwise diameter of tube 106. In this way, the elliptical shape allows the same amount of air flow (due to having the same area as the circular shape) through interior 130 of tube 106 as the circular shape of the previous embodiments.

Figure 6:
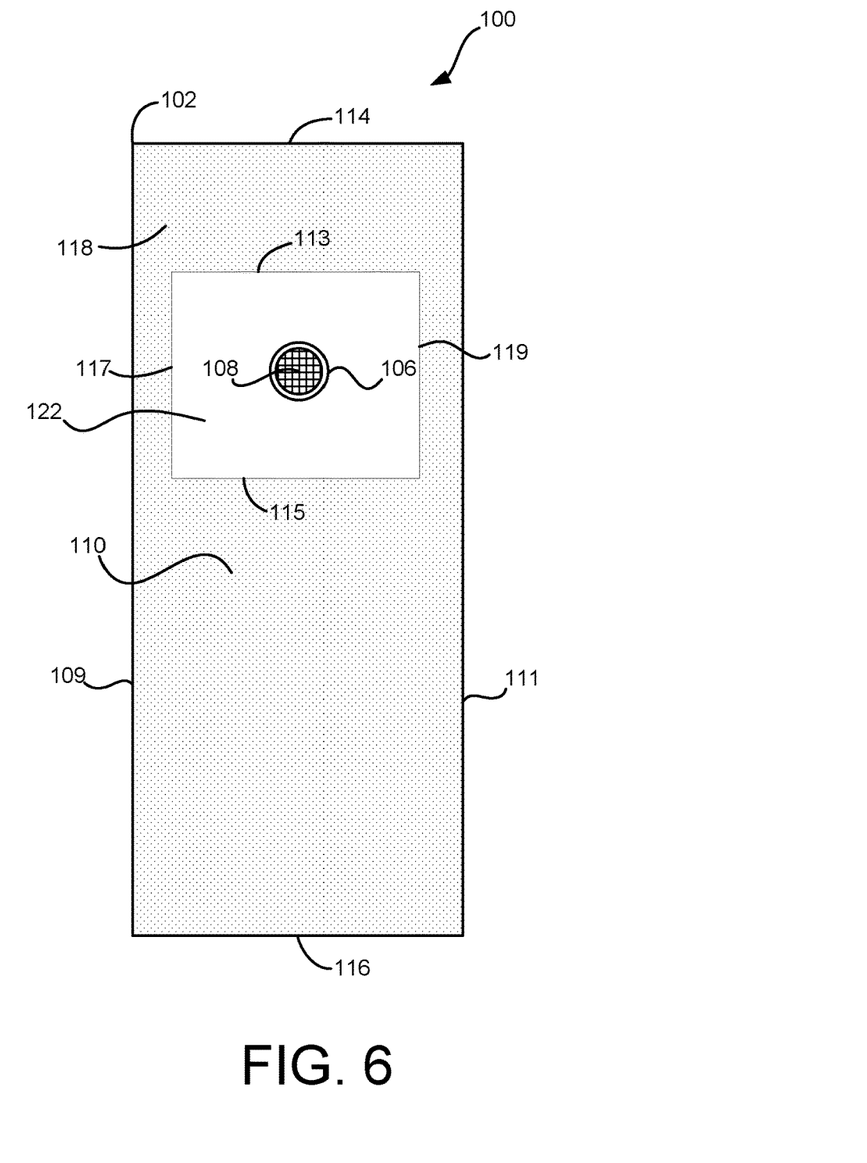
FIG. 6 is a front view of another anti-snoring device in accordance with an embodiment of the present disclosure.

Although in the embodiments described above, non-adhesive pad 122 is shown as having the same width as adhesive sheet 102, in other embodiments, the width of pad 122 may be less than the width of sheet 102. For example, referring to FIG. 6, pad 122 is shown with a shorter width from edge 117 to edge 119 than sheet 102 from edge 109 to edge 111. In this embodiment, the entire portion of side 110 of sheet 102 that is not coupled to pad 112 is configured to be adhesive. In this way, when side 110 of sheet 102 is disposed over a user's mouth, the portions of side 110 on either side or edge 117, 119 of pad 122 are configured to adhere to skin on either side of lips 3, 4 of user 1 to provide additional adhesion to device 100 when device 100 is disposed over the mouth 2 of the user 1.

In some embodiments of the present disclosure, one or more portions of device 100 may be treated with one or more substances to increase the effectiveness of device 100 while in use. For example, in some embodiments, the material on side 112 of sheet 102 may be treated with one or more scented or aromatic substances that give device 100 a pleasant, non-invasive, and sleep promoting smell to the user, such as, but not limited to, vanilla, spearmint, lavender, chamomile, bergamot, jasmine, rose, mint, sandalwood, and/or any other desired scents or aromas. In some embodiments, one or all of portions 118, 120 and/or pad 122 may be treated with one or more sleep-aiding vitamins, minerals, supplements, and/or other substances such as, but not limited to, magnesium, zinc, melatonin, valerian, kava, and/or any other sleep aiding substance. In some embodiments, one or all of portions 118, 120, and/or pad 112 may be treated with one or more substances for overcoming colds, congestion, and/or any other illness being experienced by the user that may prevent the user from sleeping restfully. Where adhesive portions 118, 120 and/or pad 122 are treated with the one or more sleep aiding substances, device 100 is configured as a transdermal patch, such that when adhesive portions 118, 120 are adhered to the skin of the user 1 and/or pad 122 comes into contact with lips 3, 4 of user 1, the one or more sleep aiding substances are delivered to the blood stream of the user 1 via the user's skin.

Figure 7:
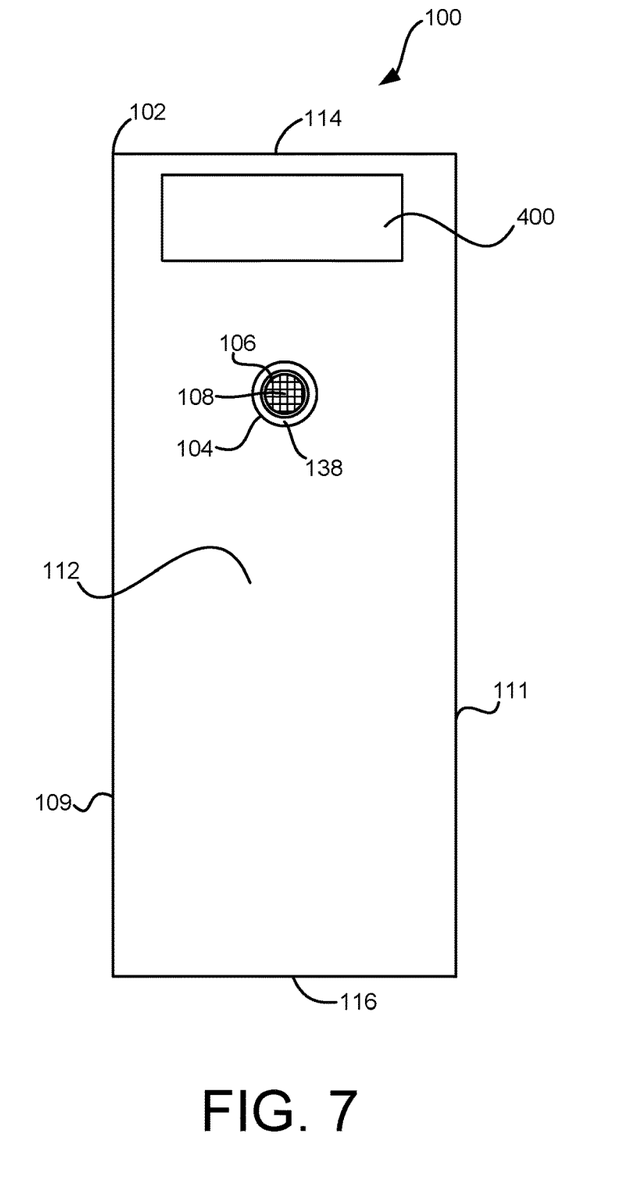
FIG. 7 is rear view of another anti-snoring device including an absorbent material in accordance with an embodiment of the present disclosure.

In some embodiments of the present disclosure, an absorbent material may be coupled to side 112 of sheet 102. For example, referring to FIG. 7, absorbent material 400 is shown coupled to side 112 of sheet 102. Absorbent material 400 is configured to be treated with one or more substances described above (e.g., to emit pleasant aromas, aid sleep, overcome illness etc.). Absorbent material 400 is disposed proximately to top end 114 of side 112, such that, when device 100 is worn by a user, material 400 is disposed proximately to the openings of the user's nose 5. In this way, while device 100 is worn by the user, the substance(s) that absorbent material is treated with are easily breathed in by the user via the user's nose 5. In some embodiments, absorbent material 400 may be pretreated with one or more substances described above. Alternatively, absorbent material 400 may be configured to absorb one or more substances applied to material 400 by a user 1 (i.e., via applying drops of liquid or otherwise to material 400) after purchase of device 100 by the user. In this way, material 400 may be treated with any substances the user 1 desires.

Figure 8:
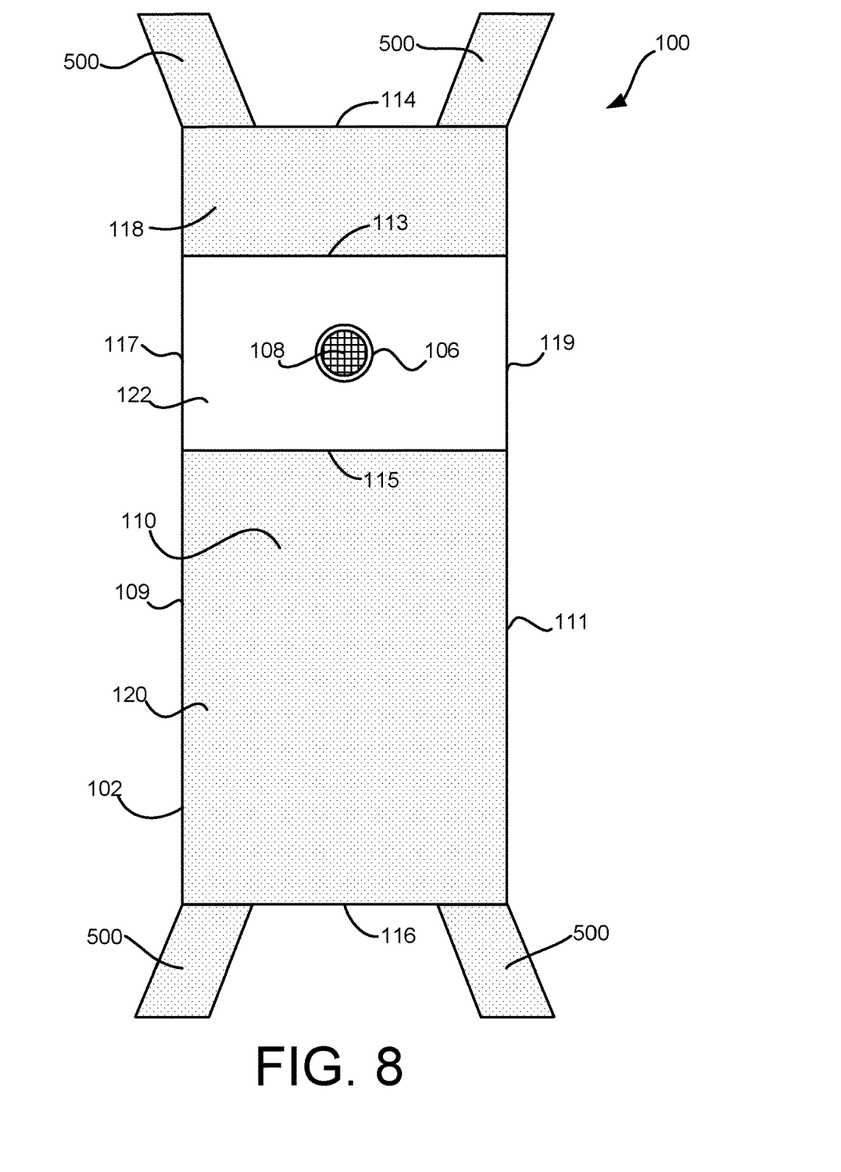
FIG. 8 is a front view of another anti-snoring device including extension members in accordance with an embodiment of the present disclosure.

Referring to FIG. 8, in one embodiment, device 100 may include one or more extension members or sheets 500 for extending the areas of the user's face that sheet 102 can adhere to. The sheet 500 are configured with adhesive backing oriented in the same direction as side 110 of sheet 102. Extension members 500 may be useful for adhering to areas on either side of the user's nose 5 and/or chin 8. In this way, if the user 1 has facial hair or other adhesive resistant conditions present on the user's face, extension members 500 may adhere to portions of the user's face that do not include hair or other obstructions. In some embodiments, extension members 500 may extend at an angle relative to edges 109, 111 of sheet 102 from ends 114, 116, as shown in FIG. 8.

It is to be appreciated that, prior to use, the device 100 includes one or more backing members coupled to the adhesive portions 118, 120 of side 110 of sheet 102. The backing members are configured to protect and preserve the adhesive coating of adhesive portions 118, 120 before device 100 is used. The backing members are configured to be removed from adhesive portions 118, 120 when device 100 is desired to be used.

It is to be appreciated that the various features shown and described are interchangeable, that is a feature shown in one embodiment may be incorporated into another embodiment.

While the disclosure has been shown and described with reference to certain preferred embodiments thereof, it will be understood by those skilled in the art that various changes in form and detail may be made therein without departing from the spirit and scope of the disclosure as defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term ' ' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed is:

1. An anti-snoring device comprising:
   an elastic sheet including a first side, a second side, and an aperture, the second side including a first adhesive portion and a second adhesive portion; and
   a tube including a first end, a second end, and a hollow interior, the first end of the tube disposed through the aperture of the elastic sheet, wherein the first end of the tube is coupled to the elastic sheet, such that the first end of the tube terminates at the first side of the elastic sheet and the second end of the tube extends a predetermined distance from the second side of the elastic sheet,
   wherein, the second side of the elastic sheet is configured to be coupled to a user's face such that the first adhesive portion adheres to skin of the user below the user's nose and above the user's upper lip, the second adhesive portion adheres to the skin of the user below the user's lower lip, and the second end of the tube extends between the user's upper lip and lower lip into the interior of the user's mouth, the predetermined distance selected such that a portion of the upper lip is parted from a portion of the lower lip and the portion of the upper lip and the portion of the lower lip are prevented from touching while the second end of the tube is disposed in the interior of the user's mouth,
   wherein, when the second side of the elastic sheet is coupled to the user's face, the elastic sheet is configured to draw the user's lower jaw toward the user's upper jaw to prevent the user from snoring while sleeping and the tube is configured with a predetermined outer circumference that enables the user's upper and lower lips to achieve a substantially closed position around the outer circumference of the tube and enables the user to breathe via the hollow interior of the tube.

2. The anti-snoring device of claim 1, further comprising a mounting disk configured to mount the first end of the tube to the elastic sheet, the mounting disk coupled to the first side of the elastic sheet and to the first end of the tube.

3. The anti-snoring device of claim 2, wherein the mounting disk includes an aperture that aligns with the hollow interior of the tube at the first end of the tube.

4. The anti-snoring device of claim 3, wherein the mounting disk includes an outer circumference, an inner circumference, and a surface oriented away from the first side of the elastic sheet, the surface including a first end at the inner circumference and a second end at the outer circumference, the surface converging toward the first side of the elastic sheet, such that the second end of the surface is disposed more proximately to the first side of the elastic sheet than the first end of the surface.

5. The anti-snoring device of claim 4, wherein the outer circumference of the mounting disk is greater than the outer circumference of the tube.

6. The anti-snoring device of claim 1, wherein when the elastic sheet is coupled to the user's face, the second adhesive portion extends over the user's chin.

7. The anti-snoring device of claim 1, wherein the elastic sheet is made of a woven fabric.

8. The anti-snoring device of claim 1, wherein the tube is configured such that the length of the tube is adjustable.

9. The anti-snoring device of claim 8, wherein the tube includes a telescoping section disposed between the first and second ends of the tube, the telescoping section configured to enable the length of the tube to be adjustable.

10. The anti-snoring device of claim 9, wherein telescoping section is configured such that the second end of the tube is pivotable relative to the first end of the tube about the telescoping section.

11. The anti-snoring device of claim 1, wherein when the anti-snoring device is worn by the user, the predetermined distance is configured such that the second end of the tube terminates at the teeth of the user.

12. The anti-snoring device of claim 1, further comprising a non-adhesive pad coupled to the second side of the elastic sheet, such that, when the second side of the elastic sheet is coupled to the user's face, the non-adhesive pad is disposed adjacent to the user's upper and lower lips.

13. The anti-snoring device of claim 12, wherein the non-adhesive pad is configured as a gauze.

14. The anti-snoring device of claim 12, wherein the non-adhesive pad includes an aperture, the tube disposed through the aperture of the non-adhesive pad.

15. The anti-snoring device of claim 1, wherein at least one of the first adhesive portion, the second adhesive portion, and/or the non-adhesive pad are treated with one or more substances configured to promote sleep.

16. The anti-snoring device of claim 1, wherein the first side of the elastic sheet is treated with one or more aromatic substances.

17. The anti-snoring device of claim 1, further comprising an air filter disposed proximately to the first end of the tube, the air filter configured to filter air breathed in through the hollow interior of the tube.

18. The anti-snoring device of claim 17, wherein the filter is a high efficiency particulate air (HEPA) filter.

19. An anti-snoring device comprising:
an elastic sheet including a first side, a second side, and an aperture, the second side including a first adhesive portion and a second adhesive portion; and
a tube including a first end, a second end, and a hollow interior, the first end of the tube disposed through the aperture of the elastic sheet, the first end of the tube is coupled to the elastic sheet, such that the first end of the tube terminates at the first side of the elastic sheet and the second end of the tube extends from the second side of the elastic sheet, wherein the tube includes a telescoping section disposed between the first and second ends of the tube and past the second side of the elastic sheet, the telescoping section configured to enable at least one of a length of the tube from the first end to the second end to be adjusted and/or the second end of the tube to be pivoted relative to the first end of the tube,
wherein, the second side of the elastic sheet is configured to be coupled to a user's face such that the first adhesive portion adheres to skin of the user below the user's nose and above the user's upper lip, the second adhesive portion adheres to the skin of the user below the user's lower lip, and the second end of the tube extends between the user's upper lip and lower lip into the user's mouth,
wherein, when the second side of the elastic sheet is coupled to the user's face, the elastic sheet is configured to maintain the user's mouth in a substantially closed position and the tube is configured to enable the user to breathe via the hollow interior of the tube to prevent the user from snoring while sleeping.

20. An anti-snoring device comprising:
an elastic sheet including a first side, a second side, and an aperture, the second side including a first adhesive portion and a second adhesive portion;
a tube including a first end, a second end, and a hollow interior, the first end of the tube disposed through the aperture of the elastic sheet, wherein the first end of the tube is coupled to the elastic sheet, such that the first end of the tube terminates at the first side of the elastic sheet and the second end of the tube extends from the second side of the elastic sheet; and
an air filter disposed proximately to the first end of the tube, the air filter terminating before the second end of the tube,
wherein, the second side of the elastic sheet is configured to be coupled to a user's face such that the first adhesive portion adheres to skin of the user below the user's nose and above the user's upper lip, the second adhesive portion adheres to the skin of the user below the user's lower lip, and the second end of the tube extends between the user's upper lip and lower lip into the user's mouth,
wherein, when the second side of the elastic sheet is coupled to the user's face, the elastic sheet is configured to maintain the user's mouth in a substantially closed position and the tube is configured to enable the user to breathe via the hollow interior of the tube to prevent the user from snoring while sleeping, the air filter configured to filter the air breathed in through the hollow interior of the tube.

* * * * *